US00PP11441P

United States Patent [19]

Kientzler

[11] Patent Number: Plant 11,441

[45] Date of Patent: Jul. 11, 2000

[54] NEW GUINEA IMPATIENS PLANT NAMED 'KIRAM'

[75] Inventor: Ludwig Kientzler, Gensingen, Germany

[73] Assignee: Paul Ecke Ranch, Encinitas, Calif.

[21] Appl. No.: 09/127,638

[22] Filed: Jul. 31, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

| | | | |
|---|---|---|---|
| P.P. 8,401 | 9/1993 | Kientzler | Plt./318 |
| P.P. 10,320 | 4/1998 | Kientzler | Plt./318 |

*Primary Examiner*—Howard J. Locker
*Assistant Examiner*—Wendy A Baker
*Attorney, Agent, or Firm*—C. A. Whealy

[57] ABSTRACT

A new and distinct cultivar of New Guinea Impatiens plant named 'Kiram', characterized by its numerous bright red-colored flowers; upright and spreading growth habit; very freely branching, dense and bushy plant habit; and dark green leaves.

1 Drawing Sheet

BACKGROUND OF THE INVENTION

The present invention relates to a new and distinct cultivar of New Guinea Impatiens plant, botanically known as *Impatiens hawkeri*, and hereinafter referred to by the cultivar name Kiram.

The new cultivar is a product of a planned breeding program conducted by the Inventor in Gensingen, Germany. The objective of the breeding program was to develop early-flowering varieties with numerous flowers, uniform plant habit, attractive flower and foliage colors, and good flower form.

The new cultivar originated from a cross made by the Inventor of the proprietary selection identified as MF 614 as the male, or pollen parent, with the proprietary selection identified as MF 73 as the female, or seed parent.

The cultivar Kiram was discovered and selected by the Inventor as a flowering plant within the progeny of the stated cross in a controlled environment in Gensingen, Germany, in April, 1996.

Asexual reproduction of the new cultivar by terminal cuttings taken at Gensingen, Germany, has shown that the unique features of this new Impatiens are stable and reproduced true to type in successive generations of asexual reproduction.

SUMMARY OF THE INVENTION

The following traits have been repeatedly observed and are determined to be the unique characteristics of 'Kiram'. These characteristics in combination distinguish 'Kiram' as a new and distinct cultivar:

1. Numerous bright red-colored flowers.
2. Upright and spreading growth habit; "V"-shaped.
3. Very freely branching, dense and bushy plant habit.
4. Dark green leaves.

Plants of the new New Guinea Impatiens are smaller and have smaller and lighter-colored flowers than plants of the male parent, the proprietary selection identified as MF 614.

Compared to plants of the female parent, the proprietary selection identified as MF 73, plants of the new New Guinea Impatiens are larger and have larger flowers and brighter flower color.

Plants of the new New Guinea Impatiens are similar in flower color to plants of the cultivar Lanai, disclosed in U.S. Plant Pat. No. 8,397. However, in side-by-side comparisons conducted in Encinitas, Calif., plants of the new New Guinea Impatiens differed from plants of the cultivar Lanai in the following characteristics:

1. Plants of the new New Guinea Impatiens are taller and more spreading than plants of the cultivar Lanai.
2. Plants of the new New Guinea Impatiens are more freely branching than plants of the cultivar Lanai.
3. Flowers of plants of the new New Guinea Impatiens are held higher above the foliage than flowers of plants of the cultivar Lanai.
4. Flowers of plants of the new New Guinea Impatiens are slightly larger than flowers of plants of the cultivar Lanai.

A detailed comparison of plants of the cultivars Kiram and Lanai appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new New Guinea Impatiens.

The photograph at the top of the sheet comprises a side perspective view of a typical plant of 'Kiram'.

The photograph at the bottom of the sheet comprises a comparison close-up view of typical flowers and leaves of the cultivars Kiram (left) and Lanai (right). Flower and foliage colors in the photographs may differ from the actual colors due to light reflectance.

DETAILED BOTANICAL DESCRIPTION

Plants of the cultivar Kiram have not been observed under all possible environmental conditions. The phenotype may vary somewhat with variations in environment such as temperature and light intensity, without, however, any variance in genotype. The following observations, measurements and comparisons describe three plants measured separately in 25-cm hanging baskets in Encinitas, Calif., under commercial practice in a polyethylene-covered greenhouse with day temperatures ranging from 21 to 32° C. and night temperatures ranging from 16 to 18° C. and light levels of about 3,500 footcandles.

In the following description, color references are made to The Royal Horticultural Society Colour Chart except where general terms of ordinary dictionary significance are used.

Classification:

*Botanical.*—*Impatiens hawkeri* cultivar Kiram.

*Commercial.*—New Guinea Impatiens cultivar Kiram.

Parentage:

*Male parent.*—Proprietary selection of *Impatiens hawkeri* identified as MF 614.

*Female parent.*—Proprietary selection of *Impatiens hawkeri* identified as MF 73.

Propagation:

*Type cutting.*—Terminal cuttings.

*Time to initiate roots.*—Summer: About 14 days with 21° C. soil temperature. Winter: About 18 days with 21° C. soil temperature.

*Time to develop roots.*—Summer: About 21 days with 21° C. soil temperature. Winter: About 24 days with 21° C. soil temperature.

Plant description:

*Plant form.*—Upright and spreading; "V"-shaped; rounded canopy.

*Growth habit.*—Vigorous. Very freely branching, dense and bushy growth. Appropriate for 10 to 25-cm containers.

*Crop time.*—From planting of a rooted cutting, about eight weeks are required to produce a finished flowering plant in a 12.5-cm container.

*Plant size.*—Height: About 28 cm. Width or spread: About 28 cm.

*Lateral branches.*—Quantity: About 12. Length: About 18 cm. Diameter: About 6.5 mm. Internode length: About 5.5 cm. Color: 59A.

*Foliage description.*—Leaves simple, generally symmetrical, abundant, opposite or in whorls, horizontal to plant. Mostly flat. Length: About 8.5 cm. Width: About 3.8 cm. Shape: Elliptic with acuminate apex, attenuate base and serrulate margin with ciliation. Texture: Smooth, glossy. Color: Young foliage, upper surface: 137A. Young foliage, lower surface: 138B. Fully expanded foliage, upper surface: 147A. Fully expanded foliage, lower surface: 147B. Venation, upper surface: 59A. Venation, lower surface: 59B. Petiole: Length: About 3.25 cm. Diameter: About 3 mm. Color: 60B.

Flower description:

*Flower type and habit.*—Bright red-colored flowers. Freely and continously flowering. Flowers arise from leaf axils. Usually about 12 flowers and flower buds per lateral branch. Flowers positioned mostly above the foliage and face mostly upward. Flowers slightly cupped and nearly rounded to rounded triangle. Flowers persistent.

*Flowering season.*—Year-round under greenhouse conditions. In the garden, flowering is continuous from spring until fall. Flowers typically last less than one week depending on environmental and cultural conditions.

*Flower size.*—Length, vertical axis: About 5.5 cm. Width, horizontal axis: About 6 cm. Depth: About 1 cm.

*Flower buds.*—Length: About 1.5 cm. Diameter: About 9 mm. Shape: Ovoid. Color: 45C.

*Petals.*—Quantity: Five. Length: Upper petal: About 2.5 cm. Middle petals: About 3 cm. Lower petals: About 3.5 cm. Width: Upper petal: About 4.2 cm. Middle petals: About 3.5 cm. Lower petals: About 3.8 cm. Shape: Cordate with acute base and entire margin. Texture: Velvety, smooth. Color: When opening, upper surface: 43A. When opening, lower surface: 44D. Fully opened, upper surface: 43A; 78C/78D at base; color does not fade. Fully opened, lower surface: 44D.

*Spur.*—Length: About 4.8 cm. Shape: Narrow and curved. Color: 59A/59B.

*Peduncles.*—Length: About 5.75 cm. Angle: Outward. Strength: Strong. Color: 59A.

*Reproductive organs.*—Androecium: Stamen number: Five, anthers fused, filaments free. Anther shape: Obovate. Anther size: 3 mm by 5 mm. Anther color: 2D. Amount of pollen: Moderate. Pollen color: 4D. Gynoecium: Five-loculate fused. Pistil length: About 6 mm. Stigma color: 4D. Ovary color: 144A.

Disease resistance: Under commercial conditions, resistance to pathogens has not been observed.

Seed development: Seed production has not been observed.

CHART A

| CHARACTERISTIC | 'KIRAM' | 'LANAI' |
|---|---|---|
| GROWTH HABIT, PLANT SHAPE | Upright and spreading | Mostly upright |
| PLANT HEIGHT | About 28 cm | About 23 cm |
| NUMBER OF LATERAL BRANCHES | About 12 | About 9 |
| LATERAL BRANCH LENGTH | About 18 cm | About 14 cm |
| INTERNODE LENGTH | About 5.5 cm | About 4 cm |
| LEAF LENGTH | About 8.5 cm | About 9.5 cm |
| LEAF WIDTH | About 3.8 cm | About 3.6 cm |
| FLOWER DIAMETER | About 5.5 by 6 cm | About 5 by 5 cm |
| PETAL COLOR, MATURE, UPPER SURFACE | 43A, 78C/78D at base | Brighter than 44A; 61B at base |
| PEDUNCLE LENGTH | About 5.75 cm | About 4.5 cm |
| PEDUNCLE COLOR | 59A | 59B |

It is claimed:

1. A new and distinct cultivar of New Guinea Impatiens plant named 'Kiram', as illustrated and described.

* * * * *

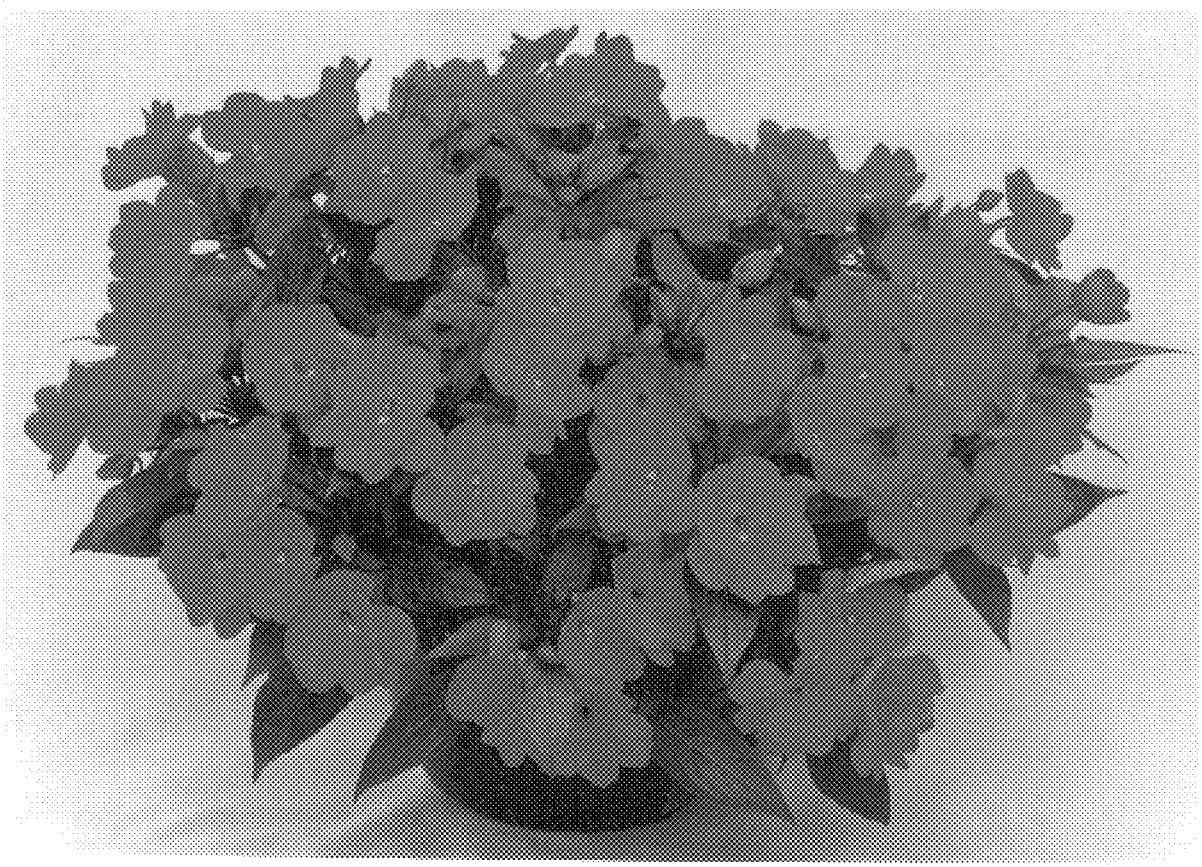
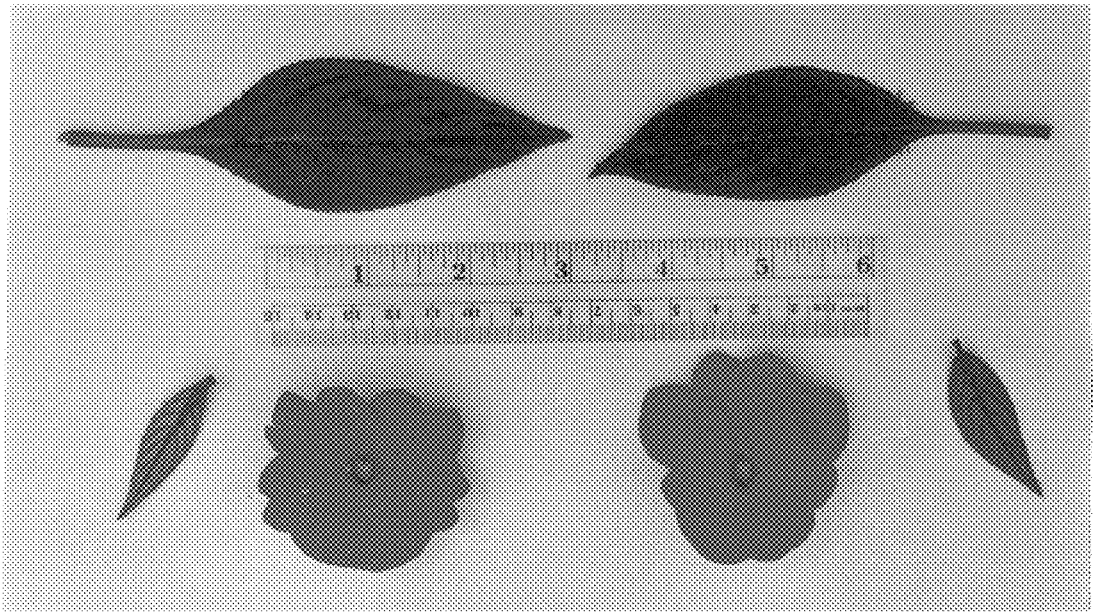
1
2
3
4
5
6